United States Patent [19]
Soma et al.

[11] Patent Number: 5,882,664
[45] Date of Patent: Mar. 16, 1999

[54] COMPOSITION FOR ENHANCING HYALURONIC ACID PRODUCTIVITY AND METHOD FOR PREPARING SAME

[75] Inventors: Tsuzuru Soma; Yoshihisa Sato, both of Yokohama, Japan

[73] Assignee: Institute For Advanced Skin Research, Inc., Kanagawa-ken, Japan

[21] Appl. No.: 904,609

[22] Filed: Aug. 1, 1997

[30] Foreign Application Priority Data

Aug. 2, 1996 [JP] Japan ................................. 8-220568

[51] Int. Cl.$^6$ ....................................................... A61K 7/48
[52] U.S. Cl. ........................................ 424/401; 424/195.1
[58] Field of Search ................................. 424/401, 195.1

[56] References Cited

FOREIGN PATENT DOCUMENTS 0531978  3/1993  European Pat. Off. .

OTHER PUBLICATIONS

Kakegawa et al., "Inhibitory Effects of Some Natural Products On The Activation Of Hyaluronidase and Their Anti-allergic Actions", Chemical and Pharmaceutical Bulletin, vol. 40, No. 6, 1992 pp. 1439–1442.

Patent Abstracts of Japan. vol. 097, No. 007, Jul. 31, 1997, & JP 09 087189 A (Ichimaru Pharcos Co Ltd), Mar. 31, 1997.

Patent Abstracts of Japan, vol. 097, No. 004, Apr. 30, 1997, & JP 08 333267 A (Maruzen Pharmaceut Co Ltd), Dec. 17, 1996.

Amin, World Patents Index, #95–317416, 1995.

*Primary Examiner*—Thurman K. Page
*Assistant Examiner*—C. Channauajjala
*Attorney, Agent, or Firm*—Wenderoth, Lind & Ponack, L.L.P.

[57] ABSTRACT

A composition for enhancing hyaluronic acid productivity particularly in epidermic cell or tissue composed of the cell, which contains an extract of a plant belonging to the family Labiatae as an active ingredient, and a process for preparation thereof. Particularly, there is provided a cosmetic or pharmaceutical composition which can be safely and directly applied to human skin to maintain the normal skin function of a juvenile.

11 Claims, No Drawings

COMPOSITION FOR ENHANCING HYALURONIC ACID PRODUCTIVITY AND METHOD FOR PREPARING SAME

BACKGROUND OF THE INVENTION

This invention relates to cosmetic and/or pharmaceutical arts. More specifically, the invention relates to a composition containing as an active ingredient an extract of a plant belonging to the family Labiatae, for enhancing hyaluronic acid productivity in a mammal, particularly tissue or cell of a human. The invention also relates to a composition for topical application to mammalian skin containing as an active ingredient an extract which is an extract of a plant belonging to the family Labiatae and first used for such a composition.

As substances having an activity to accelerate the synthesis or production of hyaluronic acid in certain cell culture tests on mammals, there have been known an extract of *Ulva pertusa,* a marine plant generally classified as a lower plant (Japanese Laid-open Patent Publication No. 9422/1994), extracts of other marine plants; for example, plants belonging to the family Ulvaceae, Gracilaria or Gelidium (Japanese Laid-open Patent Publication No. 101871/1995). Further, it is suggested that, due to the hyaluronic acid synthesis acceleration activity, these extracts bring about the activation of dermal cells, etc.

The existence of some relation between such hyaluronic acid synthesis acceleration ability and the activation of dermal cells may be accepted from the following actual situation or findings. Namely, hyaluronic acid is widely distributed in living bodies, e.g. in skin, articular liquid, corpus vitreum, ligamenta, etc., and, for example in skin, plays important roles such as the adhesion of the cells, the protection of the cells, the formation of dermal tissues, the retention of histionic water and the maintenance of flexibility. Further, in degenerative joint disease and rheumatism, hyaluronic acid generally lessens their effect and there fore injections containing hyaluronic acid itself as an active ingredient are used, and in operations of cataracta, hyaluronic acid is used as an auxiliary for the retention of aqueous chambers.

On the other hand, as symptoms of dermal aging, there can be mentioned "lowering of wetness" and "lowering of tenseness", and occurrence of "wrinkles", "flabbiness" and the like following them. Causes of these phenomena have not yet been solved completely, but as reported in Biochemica Biophysica Acta, 279: 265 (1972); Japanese Journal of Society for Cosmetic Chemists, 15: 77 (1981); Cell Structure and Function, 9: 357 (1984); Carbohydrate Research, 159: 127 (1987), etc., it is considered that dermal functions are influenced by the lowering of water content of the skin partly due to the decrease of hyaluronic acid production by dermal cells in proportion to aging.

When such actual situation or findings are taken into consideration, even if application to skin is a main object, it is desired to provide substances which are high in safety, and act directly on dermal cells and accelerate the production of hyaluronic acid in the dermal tissue more strongly. Thus, the object of the invention lies in providing substances which are superior to usual plant extracts in activity to enhance hyaluronic acid productivity in tisse or cells including human skin, and use thereof.

SUMMARY OF THE INVENTION

The present inventors have, for example, focused their attention on various culture cells derived from skin, and have made sequential researches into culture conditions therefor, and actions of various compounds or substances or compositions on qualitative or quantitative changes of various glycosaminoglycans including hyaluronic acid over the lapse of time. As a result, they found that extracts derived from plants belonging to the family Labiatae significantly enhance hyaluronic acid productivity in the cells or tissue.

Thus according to the invention, there is provided a composition for enhancing hyaluronic acid productivity in tissue or a cell in a mammal, which contains as an active ingredient an extract of any plant belonging to the family Labiatae, especially at least one plant selected from the group consisting of plants belonging to the genus Isodon, the genus Origanum, the genus Mentha, the genus Ajuga, the genus Leonurus, the genus Perilla, the genus Prunella, the genus Schizonepeta, the genus Rosmarinus, the genus Scutellaria, the genus Lavandula, the genus Ocimum, the genus Thymus and the genus Salvia among the family Labiatae.

In order to attain the object of the invention, the composition comprises the plant extract in an amount enough to accelerate the production of hyaluronic acid in a cell or tissue of a mammal, and cosmetically or pharmaceutically acceptable carriers, diluents or auxiliaries.

Further, according to the invention, there is also provided a method for enhancing hyaluronic acid productivity in a cell of tissue of a mammal, which comprises percutaneously administering the composition.

Further, there is also provided use of the plant extract for preparing a composition for enhancing hyaluronic acid productivity in tissue or a cell in a mammal.

Further, there is also provided a process for preparing a composition for enhancing hyaluronic acid productivity in tissue or a cell in a mammal, which comprises mixing the plant extract homogeneously with cosmetically or pharmaceutically acceptable carriers, diluents or auxiliaries.

Under the consideration of the above-mentioned actual situations of use and findings on hyaluronic acid, the composition for enhancing hyaluronic acid productivity according to the invention can be used in such a form that it is made to be contained in articular liquors, etc. of mammals, but especially, it can preferably be used for enhancing hyaluronic acid productivity in human epidermic cells or tissues composed of the cells.

Incidentally, among the above plant extracts, an extract of at least one plant selected from the group consisting of *Mentha viridis* L. and *Mentha suaveolens* belonging to the genus Mentha, *Ajuga reptans* belonging to the genus Ajuga, *Leonurus macranthus* Maxim, belonging to the genus Leonurus, and *Perilla frutescens* Britton var. *japonica* Hara and *Perilla frutescens* Britton var. *citriodora* Ohwi belonging to the genus Perilla, of course, shows an activity to enhance the productivity significantly, but the use of such a plant extract for a composition for topical application to mammalian skin has not yet been known. Thus according to the invention, there is also provided a novel composition for topical application to mammalian skin which contains an extract of a plant belonging to such a specific species, but is not limited to an activity to enhance the productivity.

DETAILED DESCRIPTION OF THE INVENTION

As specific examples of plants belonging to the specific genera of the family "Labiatae", there can be mentioned the following plants and plant bodies, respectively.

As plants belonging to the genus Isodon, there can be used the whole herb of *Isodon japonicus* Hara, the part on the ground of *Isodon trichocarous* Kudo, etc. As plants belonging to the genus Origanum, there can be used the whole herb of *Origanum majorana* L., etc. As plants belonging to the genus Mentha, there can be used the whole herb of *Mentha piperita* L., the whole herb of *Mentha viridis* L., the whole herb of *Mentha suaveolens,* etc.

As plants belonging to the genus Ajuga, there can be used the whole herb of *Ajuga decumbens* Thunb., the whole herb of *Ajuga reptans,* etc. As plants belonging to the genus Leonurus, there can be used the whole herb and the seed of *Leonurus sibiricus* Linne, the whole herb of Leonurus macranthus Maxim, etc. As plants belonging to the genus Perilla, there can be used the whole herb and the seed of *Perilla frutescens* Britton var. *acuta* Kudo, the whole herb and the seed of *Perilla frutescens* Britton var. *acuta* Kudo forma *viridis* Makino, the whole herb and the seed of *Perilla frutescens* Britton var. *crispa* Decne, the whole herb of *Perilla frutescens* Britton var. *japonica* Hara, the leaves and stems *Perilla frutescens* Britton var. *citriodora* Ohwi, etc.

As plants belonging to the genus Prunella, there can be used the spikes of *Prunella vulgaris* L. var. *lilacina* Nakai, etc. As plants belonging to the genus Schizonepeta, there can be used the whole herb of *Schizonepeta tenuifolia* Briquet, etc. As plants belonging to the genus Rosmarinus, there can be used the whole herb of *Rosmarinus officinalis* Linne, etc. As plants belonging to the genus Scutellaria, there can be used the roots of *Scutellaria baicalensis* Georgi, the whole herb of *Scutellaria indica* L., etc.

As plants belonging to the genus Lavandula, there can be used the whole herb of *Lavandula angustifolia* Moench., etc. As plants belonging to the genus Ocimum, there can be used the leaves and stems of *Ocimum basillicum* L., and the whole herb of *Ocimum scanctum,* etc. As plants belonging to genus Thymus, there can be used the whole herb of *Thymus vulgaris* L., the whole herb of *Thymus quinquecostatus* Celak., etc. As plants belonging to the genus Salvia, there can be used the leaves and stems of *Salvia officinalis* L., the roots of *Salvia miltiorrhiza* Bunge, etc.

When an extract according to the invention is prepared, the plant body can be in an undried state, but it is preferred in view of extraction efficiency to use it for extraction after it was dried by a method such as air drying, drying with heating or freeze drying. There is no limitation in methods for extracting the substances of the invention, usual extraction methods can be adopted, and such methods can be carried out using water, aqueous hydrophilic organic solvents, organic solvents, etc. which are used in the preparation of plant extracts known per se.

The amount of a plant extract according to the invention is namely the amount enough to accelerate the production of hyaluronic acid in a cell or tissue of a mammal, 0.0001 to 20% by weight, preferably 0.005 to 5% by weight as dried matter based on the whole weight of the composition. When the amount is under 0.0001% by weight, the effects of the invention cannot be obtained sufficiently, and when it is above 20% by weight, it is not suitable for formulation. When an extract solution is blended, the amount to be used is 0.004 to 100% by 30 volume, preferably 0.2 to 100% by volume. When the amount is under 0.004% by volume, the effects of the invention cannot be exhibited sufficiently. Doses necessary for accelerating the production of hyaluronic acid are described later.

Said amount can be composed of at least one of the above extracts, namely one of the plant extracts, or plant extracts derived from two or more of species of the same genus or two or more extracts derived from plants belonging to different genera.

The composition for enhancing hyaluronic acid productivity and the composition for topical application to mammalian skin of the invention can contain, besides the above extract as an active ingredient, various cosmetically or pharmaceutically acceptable carriers, diluents or auxiliaries, or other active compounds, respectively alone or in combination, within such a range that the efficacy of the active ingredient is not badly influenced. When, for example, a composition for topical application to skin or external composition for skin is meant to be prepared, as such additives used as carriers, diluents or auxiliaries, there can be mentioned components usually used for external compositions for skin, for example surfactants, oils, alcohols, humectants, vitamins, thickeners, antiseptics, antioxidants, chelating agents, pH-adjusting agents, perfumes, colorants, ultraviolet absorbers, ultraviolet-scattering agents, amino acids, skin function accelerators, hormones, skin activators, water, etc.

Specifically, there can be mentioned surfactants such as nonionic surfactants, anionic surfactants and cationic surfactants, hydrocarbons such as solid or liquid paraffins, crystal oils, ceresine, ozocerite and montan wax, vegetable or animal fats and oils and waxes such as silicone oils, olive oil, earth wax, carnauba wax and lanolin, fatty acids or their esters such as stearic acid, palmitic acid, oleic acid, glycerol monostearate, glycerol monooleate, isopropyl myristate and isopropyl stearate, esters between branched fatty acids and monohydric or polyhydric alcohols, alcohols such as ethyl alcohol, isopropyl alcohol, cetyl alcohol and palmityl alcohol, polyalcohols such as glycol, glycerol and sorbitol, or their esters, etc.

Further, there can also be mentioned amino acids such as arginine, serine and methionine, vitamins such as vitamin A acid, vitamin $B_6$, ascorbic acid and its derivatives, vitamin D and its derivatives, vitamin E and its derivatives, and biotin, polysaccharides, cholesterols, pantothenic acid and its derivatives, glycyrrhizin and its derivatives, glycyrrhetinic acid and its derivatives, nicotinic esters such as benzyl nicotinate, antiseptics such as ethylparaben and butylparaben, antioxidants such as butylhydroxytoluene and propyl gallate, skin whitening agents such as arbutin and kojic acid, skin function enhancers such as placenta extract and cepharanthine, female hormones such as estradiol, retinol, alphahydroxylic acid and its alkyl esters, etc.

The composition for enhancing hyaluronic acid productivity according to the invention has an excellent in vivo hyaluronic acid productivity enhancement action and has great safety, and thus it can be used for various uses such as the above-mentioned medicaments or quasi-drugs, or cosmetics. As the forms or states thereof in use as an external composition for skin, any forms or states can be utilized so long as they are forms or states capable of being applied to integumentum commune, such as liquids, emulsions, creams, ointments, sticks, packs, pastes and powders. The external composition for skin of the invention is fit for an administration method through percutaneous administration wherein it is applied onto, stuck on or sprayed on skin (particularly human skin).

The dose of the composition for enhancing hyaluronic acid productivity of the invention cannot definitely be prescribed because it varies depending on age, difference between individuals, the conditions of diseases, etc., but in general, its dose in the case where it is administered to humans is 0.01 to 100 mg, preferably 0.1 to 50 mg per kg of body weight per day, and the dose can be administered once a day or in divided doses two to four times a day.

By such administration, the production of hyaluronic acid in a cell or tissue of a mammal, especially a human can be accelerated. Thus, for example, the lowering of dermal functions caused by dermal aging can be prevented.

The preparation process of the substances of the invention and their hyaluronic acid productivity enhancement activities are more specifically described below according to examples, but the invention should not be limited thereby. (Preparation process)

As for a general preparation process of a plant extract used in the invention, it can be obtained by extracting the plant body with water, or aqueous alcohols containing lower alcohols such as methanol, ethanol and isopropanol, or aqueous alcohols containing polyhydric alcohols such as propylene glycol and 1,3-butylene glycol, or acetone, methyl ethyl ketone, acetonitrile, dimethyl sulfoxide, hydrocarbons such as hexane, chlorinated carbons such as chloroform, etc., for example of 0 to 100° C. The ratio between water and the alcohol in the aqueous alcohol is preferably 1:99 to 100:0, more preferably 10:90 to 100:0 as a volume ratio of the alcohol : water.

Preparation example 1

One liter of 50% aqueous ethanol solution was added to 100 g of the dried whole herb of *Isodon japonicus* Hara, the mixture was refluxed for extraction on a water bath of 80° C. for 4 hours, and the extraction filtrate was concentrated and dried to give 18.7 g of an extract of *Isodon japonicus* Hara. In the same manner as above, extracts were obtained as filtrates, concentrated solutions or dry powders, at yields shown in Table I, using extraction solvents and plants shown in Table I.

TABLE I

| Preparation example | Plant body | Extraction solvent | Yield (g) |
|---|---|---|---|
| 2 | *Origanum majorana* L. | 50% aqueous ethanol solution | 23.8 |
| 3 | *Mentha piperita* L. | 50% aqueous ethanol solution | 22.9 |
| 4 | *Mentha viridis* L. | 50% aqueous ethanol solution | 24.1 |
| 5 | *Mentha suaveolens* | 50% aqueous ethanol solution | 16.4 |
| 6 | *Ajuga decumbens* Thunb. | 50% aqueous ethanol solution | 18.3 |
| 7 | *Ajuga reptans* | 50% aqueous ethanol solution | 20.6 |
| 8 | *Leonurus sibiricus* Linne | 30% aqueous ethanol solution | 17.2 |
| 9 | *Leonurus macranthus* Maxim. | 50% aqueous ethanol solution | 20.3 |
| 10 | *Perilla frutescens* Britton var. acuta Kudo | 35% aqueous ethanol solution | 19.2 |
| 11 | *Perilla frutescens* Britton var. acuta Kudo forma viridis Makino | 35% aqueous ethanol solution | 18.7 |
| 12 | *Perilla frutescens* Britton var. crispa Decne | 35% aqueous ethanol solution | 17.9 |
| 13 | *Perilla frutescens* Britton var. japonica Hara | 70% aqueous ethanol solution | 25.5 |
| 14 | *Perilla frutescens* Britton var. citriodora Ohwi*[1) | 70% aqueous ethanol solution | 22.1 |
| 15 | *Prunella vulgaris* L. var. lilacina Nakai*[2) | 30% aqueous butylene glycol solution | (Solution) |
| 16 | *Schizonepeta tenuifolia* Briquet | 50% aqueous ethanol solution | 21.6 |
| 17 | *Rosmarinus officinalis* Linne | 45% aqueous butylene glycol solution | (Solution) |
| 18 | *Scutellaria baicalensis* | 50% aqueous ethanol solution | 22.4 |
| 19 | *Lavandula angustifolia* Moench. | 50% aqueous ethanol solution | 20.9 |
| 20 | *Ocimum basillicum* L.*[1) | 50% aqueous ethanol solution | 24.3 |

TABLE I-continued

| Preparation example | Plant body | Extraction solvent | Yield (g) |
|---|---|---|---|
| 21 | *Ocimum scanctum* | 50% aqueous ethanol solution | 20.5 |
| 22 | *Thymus vulgaris* L. | 10% aqueous ethanol solution | 17.6 |
| 23 | *Salvia officinalis* L.*[1) | 45% aqueous propylene glycol solution | (Solution) |

*[1):Leaves and stems
*[2):Flower Spikes
*[3):Roots
Others are whole herbs

Hyaluronic Acid Production Acceleration Test

Keratinocytes derived from normal human skin (NHEK) were cultured in a serum-free medium. This cell is frequently used for examining the physiological activities of human epidermic keratinocytes, and fit for examining hyaluronic acid productivity. $5\times10^3$ NHEK cells were sowed in each of wells each having a diameter of 15.6 mm (24-hole plates), and cultured at 37° C. for 3 days using the serum-free medium. After 3 days culture, the medium was replaced by a serum-free medium containing 0 to 2% an extract shown in Preparation examples, and culture was continued. After 7 days culture, the culture supernatants were taken and assayed for hyaluronic acid concentrations, respectively. The test was carried out in triplicate, and average values were calculated.

The hyaluronic acid concentration of each of the culture broths was assayed according to a sandwich binding assay using a hyaluronic acid binding protein (HABP) (Rinsho Byori (Clinical Pathology), 36:536, 1991; Biochemical Journal, 309: 649–656, 1995; Ensho (Inflammation), 16:97, 1996). The hyaluronic acid concentration in the culture broth of the control example not containing any test substance was assayed at the same time, and the hyaluronic acid concentration of the test example induced by the addition of a test substance was divided by the hyaluronic acid concentration of the control example to give hyaluronic acid productivity.

Test example 1

The hyaluronic acid concentrations of the serum-free culture broths containing 0 to 0.1% the *Isodon japonicus* Hara extract of Preparation example 1 were assayed, and each of the average values was divided by the average value of the hyaluronic acid concentrations of the serum-free culture broths not containing the *Isodon japonicus* Hara extract (control example) to give hyaluronic acid production acceleration ability. The results are shown in the following Table II.

TABLE II

| Test substance | Concentration in the culture broth (w/v) | Hyaluronic acid production acceleration ability |
|---|---|---|
| *Isodon japonicus* Hara extract | 0% (control example) | 1.0 |
| | 0.005% (50 µg/ml) | 1.2 |
| | 0.01% (100 µg/ml) | 1.6 |
| | 0.025% (250 µg/ml) | 2.7 |
| | 0.05% (500 µg/ml) | 4.2 |
| | 0.1% (1 mg/ml) | 3.5 |

In the same manner as in Test example 1, the hyaluronic acid production acceleration ability of the extract of each Preparation example was determined. The results are shown in Table III.

TABLE III

| Test example | Test substance | Concentration in the culture broth (w/v) | Hyaluronic acid production acceleration ability |
|---|---|---|---|
| 2 | *Origanum majorana* L. extract | 0.025% | 2.8 |
| 3 | *Mentha piperita* L. extract | 0.025% | 3.4 |
| 4 | *Mentha viridis* L. extract | 0.025% | 4.5 |
| 5 | *Mentha suaveolens* extract | 0.025% | 2.9 |
| 6 | *Ajuga decumbens* Thunb. extract | 0.025% | 3.3 |
| 7 | *Ajuga reptans* extract extract | 0.025% | 2.9 |
| 8 | *Leonurus sibiricus* Linne extract | 0.025% | 2.4 |
| 9 | *Leonurus macranthus* Maxim. extract | 0.025% | 2.1 |
| 10 | *Perilla frutescens* Britton var. acuta Kudo extract | 0.025% | 3.4 |
| 11 | *Perilla frutescens* Britton var. acuta Kudo forma viridis Makino extract | 0.025% | 3.2 |
| 12 | *Perilla frutescens* Britton var. crispa Decne extract | 0.025% | 2.8 |
| 13 | *Perilla frutescens* Britton var. japonica Hara extract | 0.05% | 2.7 |
| 14 | *Perilla frutescens* Britton var. citriodora Ohwi extract | 0.05% | 2.5 |
| 15 | *Prunella vulgaris* L. var. lilacina Nakai extract | 1*:99 (v:v) | 1.8 |
| 16 | *Schizonepeta tenuifolia* Briquet extract | 0.025% | 3.1 |
| 17 | *Rosmarinus officinalis* Linne extract | 1*:99 (v:v) | 2.4 |
| 18 | *Scutellaria baicalensis* Georgi extract | 0.025% | 3.5 |
| 19 | *Lavandula angustifolia* Moench. extract | 0.05% | 3.0 |
| 20 | *Ocimum basillicum* L. extract | 0.05% | 2.8 |
| 21 | *Ociumum scanctum* extract | 0.025% | 2.3 |
| 22 | *Thymus vulgaris* L. extract | 0.05% | 2.8 |
| 23 | *Salvia officinalis* L. extract | 1*:99 (v:v) | 4.2 |

*:The extract solution was applied as such

As understood from the foregoing, the plant extracts according to the invention have excellent hyaluronic acid production acceleration ability or hyaluronic acid productivity enhancement effect in human keratinocytes. Further, these plant extracts did not give any damage to the cells in these test examples, and thus also had extremely high safety.

There are mentioned below examples of formulation in the case where the plant extracts according to the invention are used as external compositions for mammalian skin or composition for topical application to mammalian skin for enhancing hyaluronic acid productivity especially in epidermic cells or tissues containing the cells.

| Formulation example 1 (Ointment) | |
|---|---|
| (1) *Perilla frutescens* Britton var. japonica Hara extract (the one obtained in Preparation example 13) | 1.0% |
| (2) Plastibase ® 50W (Bristol Myers - Squib) | 99.0 |
| Total | 100.0% |

(1) was kneaded into (2) composed of liquid paraffin (95%) and polyethylene (5%), and the mixture was deaerated by reduced pressure to give an ointment.

| Formulation example 2 (Cream) | |
|---|---|
| A. Cetanol | 4.0% |
| Vaseline | 7.0 |
| Isopropyl myristate | 8.0 |
| Squalane | 12.0 |
| Dimethylpolysiloxane | 3.0 |
| Glycerol monostearate | 2.2 |
| POE(20)sorbitan monostearate | 2.8 |
| Glycyrrhetinic acid stearate | 0.02 |
| Ethylparaben | 0.1 |
| Butylparaben | 0.1 |
| B. Aqueous phase | |
| *Perilla frutescens* Britton var. acuta Kudo extract (the one obtained in Preparation example 10) | 0.1 |
| 1,3-Butylene glycol | 7.0 |
| Phenoxyethanol | 0.2 |
| Ascorbic acid phosphate ester magnesium salt | 4.0 |
| Purified water | Balance |
| Total | 100.0% |

The *Perilla frutescens* Britton var. *acuta* Kudo extract was dissolved in 1,3-butylene glycol under heating, phenoxyethanol and ascorbic acid phosphate ester magnesium salt were added, and the mixture was held at 70° C. to give Phase B. Phase A as a solution by heating to 70° C. was added to Phase B under stirring, homomixer treatment was carried out to make the emulsified particles small, and the mixture was rapidly cooled under stirring to give a cream.

| Formulation example 3 (Lotion) | |
|---|---|
| A. *Isodon japonicus* Hara extract (the one obtained in Preparation example 1) | 0.5% |
| Ethanol | 7.0 |
| Polyoxyethylene (20) oleyl ether | 0.5 |
| Methylparaben | 0.05 |
| B. Glycerol | 4.0 |
| 1,3-Butylene glycol | 4.0 |
| Citric acid | 0.01 |
| Sodium citrate | 0.1 |
| Purified water | Balance |
| Total | 100.0% |

Phase A as a solution in ethanol was added to Phase B as a solution in purified water to solubilize the former, and the solution was filtered to give a lotion.

| Formulation example 4 (Paste) | |
|---|---|
| *Scutellaria baicalensis* Georgi extract (the one obtained in Preparation example 18) | 2.0% |
| Zinc oxide | 30.0 |
| Starch | 30.0 |
| White petrolatum | 38.0 |
| Total | 100.0% |

Part of White petrolatum was melted on a water bath, the *Scutellaria baicalensis* Georgi extract was added, zinc oxide sieved and starch were kneaded there-into, the residual White petrolatum was added, and the mixture was sufficiently kneaded to give a homogeneous paste.

| Formulation example 5 (Cream) | |
|---|---|
| A. Cetanol | 4.0% |
| Vaseline | 7.0 |
| Isopropyl myristate | 8.0 |
| Squalane | 12.0 |
| Dimethylpolysiloxane | 3.0 |
| Glycerol monostearate | 2.2 |
| POE(20)sorbitan monostearate | 2.8 |
| Glycyrrhetinic acid stearate | 0.02 |
| Ethylparaben | 0.1 |
| Butylparaben | 0.1 |
| B. Aqueous phase | |
| *Schizonepeta tenuifolia* Briquet extract (the one obtained in Preparation example 16) | 0.1 |
| 1,3-Butylene glycol | 7.0 |
| Phenoxyethanol | 0.2 |
| Ascorbic acid phosphate ester magnesium salt | 4.0 |
| Purified water | Balance |
| Total | 100.0% |

The *Schizonepeta tenuifolia* Briquet extract was dissolved in 1,3-butylene glycol under heating, phenoxyethanol and ascorbic acid phosphate ester magnesium salt were added, and the mixture was held at 70° C. to give Phase B. Phase A as a solution by heating to 70° C. was added to Phase B under stirring, homomixer treatment was carried out to make the emulsified particles small, and the mixture was rapidly cooled under stirring to give a cream.

| Formulation example 6 (Cream) | |
|---|---|
| A. Cetano | 14.0% |
| Vaseline | 7.0 |
| Isopropyl myristate | 8.0 |
| Squalane | 12.0 |
| Dimethylpolysiloxane | 3.0 |
| Glycerol monostearate | 2.2 |
| POE(20)sorbitan monostearate | 2.8 |
| Glycyrrhetinic acid stearate | 0.02 |
| Ethylparaben | 0.1 |
| Butylparaben | 0.1 |
| B. Aqueous phase | |
| *Mentha viridis* L. extract (the one obtained in Preparation example 4) | 0.1 |
| *Ajuga reptans* extract (the one obtained in Preparation example 7) | 0.1 |
| *Leonurus macranthus* Maxim. extract (the one obtained in Preparation example 9) | 0.1 |
| 1,3-Butylene glycol | 7.0 |
| Phenoxyethanol | 0.2 |
| Ascorbic acid phosphate ester magnesium salt | 4.0 |
| Purified water | Balance |
| Total | 100.0% |

The Mentha viridis L. extract, the *Ajuga reptans* extract and the Leonurus macranthus Maxim. extract were dissolved in 1,3-butylene glycol under heating, phenoxyethanol and ascorbic acid phosphate ester magnesium salt were added, and the mixture was held at 70° C. to give Phase B. Phase A as a solution by heating to 70° C. was added to Phase B under stirring, homomixer treatment was carried out to make the emulsified particles small, and the mixture was rapidly cooled under stirring to give a cream.

| Formulation example 7 (Cream) | |
|---|---|
| A. Cetanol | 4.0% |
| Vaseline | 7.0 |
| Isopropyl myristate | 8.0 |
| Squalane | 12.0 |
| Dimethylpolysiloxane | 3.0 |
| Glycerol monostearate | 2.2 |
| POE(20)sorbitan monostearate | 2.8 |
| Glycyrrhetinic acid stearate | 0.02 |
| Ethylparaben | 0.1 |
| Butylparaben | 0.1 |
| B. Aqueous phase | |
| *Mentha suaveolens* extract (the one obtained in Preparation example 5) | 0.1 |
| *Ajuga decumbens* Thunb. extract (the one obtained in Preparation example 6) | 0.1 |
| *Perilla frutescens* Britton var. citriodora Ohwi extract (the one obtained in Preparation example 14) | 0.1 |
| 1,3-Butylene glycol | 7.0 |
| Phenoxyethanol | 0.2 |
| Ascorbic acid phosphate ester magnesium salt | 4.0 |
| Purified water | Balance |
| Total | 100.0% |

The Mentha suaveolens extract, the *Ajuga decumbens* Thunb. extract and the *Perilla frutescens* Britton var. *citriodora* Ohwi extract were dissolved in 1,3-butylene glycol under heating, phenoxyethanol and ascorbic acid phosphate ester magnesium salt were added, and the mixture was held at 70° C. to give Phase B. Phase A as a solution by heating to 70° C. was added to Phase B under stirring, homomixer treatment was carried out to make the emulsified particles small, and the mixture was rapidly cooled under stirring to give a cream.

| Formulation example 8 (Lotion) | |
|---|---|
| A. *Origanum majorana* L. extract (the one obtained in Preparation example 2) | 0.5% |
| Ethanol | 7.0 |
| Polyoxyethylene (20) oleyl ether | 0.5 |
| Methylparaben | 0.05 |
| B. Glycerol | 4.0 |
| 1,3-Butylene glycol | 4.0 |
| Citric acid | 0.01 |
| Sodium citrate | 0.1 |
| Purified water | Balance |
| Total | 100.0% |

Phase A as a solution in ethanol was added to Phase B as a solution in purified water to solubilize the former, and the solution was filtered to give a lotion.

| Formulation example 9 (Lotion) | |
|---|---|
| A. *Mentha piperita* L. extract (the one obtained in Preparation example 3) | 0.5% |
| *Leonurus sibiricus* Linne extract (the one obtained in Preparation example 8) | 0.5 |
| Ethanol | 7.0 |
| Polyoxyethylene (20) oleyl ether | 0.5 |
| Methylparaben | 0.05 |
| B. Glycerol | 4.0 |
| 1,3-Butylene glycol | 4.0 |

| Formulation example 9 (Lotion) | |
| --- | --- |
| Citric acid | 0.01 |
| Sodium citrate | 0.1 |
| Purified water | Balance |
| Total | 100.0% |

Phase A as a solution in ethanol was added to Phase B as a solution in purified water to solubilize the former, and the solution was filtered to give a lotion.

| Formulation example 10 (Lotion) | |
| --- | --- |
| A. *Perilla frutescens* Britton var. acuta Kudo forma viridis Makino extract (the one obtained in Preparation example 11) | 0.5% |
| *Perilla frutescens* Britton var. crispa Decne extract (the one obtained in Preparation example 12) | 0.5 |
| Ethanol | 7.0 |
| Polyoxyethylene (20) oleyl ether | 0.5 |
| Methylparaben | 0.05 |
| B. Glycerol | 4.0 |
| 1,3-Butylene glycol | 4.0 |
| Citric acid | 0.01 |
| Sodium citrate | 0.1 |
| Purified water | Balance |
| Total | 100.0% |

Phase A as a solution in ethanol was added to Phase B as a solution in purified water to solubilize the former, and the solution was filtered to give a lotion.

| Formulation example 11 (Cream) | |
| --- | --- |
| A. Cetanol | 4.0% |
| Vaseline | 7.0 |
| Isopropyl myristate | 8.0 |
| Squalane | 12.0 |
| Dimethylpolysiloxane | 3.0 |
| Glycerol monostearate | 2.2 |
| POE(20)sorbitan monostearate | 2.8 |
| Glycyrrhetinic acid stearate | 0.02 |
| Ethylparaben | 0.1 |
| Butylparaben | 0.1 |
| B. Aqueous phase | |
| *Prunella vulgaris* L. var. lilacina Nakai extract (the one obtained in Preparation example 15) | 0.1 |
| *Rosmarinus officinalis* Linne extract (the one obtained in Preparation example 17) | 0.2 |
| 1,3-Butylene glycol | 7.0 |
| Phenoxyethanol | 0.2 |
| Ascorbic acid phosphate ester magnesium salt | 4.0 |
| Purified water | Balance |
| Total | 100.0% |

The *Prunella vulgaris* L. var. *lilacina* Nakai extract and the *Rosmarinus officinalis* Linne extract were dissolved in 1,3-butylene glycol under heating, phenoxyethanol and ascorbic acid phosphate ester magnesium salt were added, and the mixture was held at 70° C. to give Phase B. Phase A as a solution by heating to 70° C. was added to Phase B under stirring, homomixer treatment was carried out to make the emulsified particles small, and the mixture was rapidly cooled under stirring to give a cream.

| Formulation example 12 (Lotion) | |
| --- | --- |
| A. *Lavandula angustifolia* Moench. extract (the one obtained in Preparation example 19) | 0.5% |
| *Ocimum basillicum* L. extract (the one obtained in Preparation example 20) | 0.5 |
| *Ocimum scanctum* extract (the one obtained in Preparation example 21) | 0.5 |
| Ethanol | 7.0 |
| Polyoxyethylene (20) oleyl ether | 0.5 |
| Methylparaben | 0.05 |
| B. Glycerol | 4.0 |
| 1,3-Butylene glycol | 4.0 |
| Citric acid | 0.01 |
| Sodium citrate | 0.1 |
| Purified water | Balance |
| Total | 100.0% |

Phase A as a solution in ethanol was added to Phase B as a solution in purified water to solubilize the former, and the solution was filtered to give a lotion.

| Formulation example 13 (Lotion) | |
| --- | --- |
| A. *Thymus vulgaris* L. extract (the one obtained in Preparation example 22) | 0.5% |
| Ethanol | 7.0 |
| Polyoxyethylene (20) oleyl ether | 0.5 |
| Methylparaben | 0.05 |
| B. Glycerol | 4.0 |
| 1,3-Butylene glycol | 4.0 |
| Citric acid | 0.01 |
| Sodium citrate | 0.1 |
| Purified water | Balance |
| Total | 100.0% |

Phase A as a solution in ethanol was added to Phase B as a solution in purified water to solubilize the former, and the solution was filtered to give a lotion.

| Formulation example 14 (Cream) | |
| --- | --- |
| A. Cetanol | 4.0% |
| Vaseline | 7.0 |
| Isopropyl myristate | 8.0 |
| Squalane | 12.0 |
| Dimethylpolysiloxane | 3.0 |
| Glycerol monostearate | 2.2 |
| POE(20)sorbitan monostearate | 2.8 |
| Glycyrrhetinic acid stearate | 0.02 |
| Ethylparaben | 0.1 |
| Butylparaben | 0.1 |
| B Aqueous phase | |
| *Salvia officinalis* L. extract (the one obtained in Preparation example 23) | 0.1 |
| 1,3-Butylene glycol | 7.0 |
| Phenoxyethanol | 0.2 |
| Ascorbic acid phosphate ester magnesium salt | 4.0 |
| Purified water | Balance |
| Total | 100.0% |

The *Salvia officinalis* L. extract was dissolved in 1,3-butylene glycol under heating, phenoxyethanol and ascorbic acid phosphate ester magnesium salt were added, and the mixture was held at 70° C. to give Phase B. Phase A as a solution by heating to 70° C. was added to Phase B under stirring, homomixer treatment was carried out to make the emulsified particles small, and the mixture was rapidly cooled under stirring to give a cream.

What is claimed is:

1. A composition for enhancing hyaluronic acid productivity in a cell or tissue of a mammal, which comprises an extract of at least one plant belonging to the family Labiatae in an amount enough to accelerate the production of hyaluronic acid, and cosmetically or pharmaceutically acceptable carriers, diluents or auxiliaries.

2. The composition according to claim 1 wherein the plant belonging to the family Labiatae is at least one selected from the group consisting of plants belonging to the genus Isodon, the genus Origanum, the genus Mentha, the genus Ajuga, the genus Leonurus, the genus Perilla, the genus Prunella, the genus Schizonepeta, the genus Rosmarinus, the genus Scutellaria, the genus Lavandula, the genus Ocimum, the genus Thymus and the genus Salvia.

3. The composition according to claim 2 wherein the plants belonging to the genus Isodon are *Isodon japonicus* Hara and *Isodon trichocarous* Kudo, the plant belonging to the genus Origanum is *Origanum majorana* L., the plants belonging to the genus Mentha are *Mentha piperita* L., *Mentha viridis* L. and *Mentha suaveolens,* the plants belonging to the genus Ajuga are *Ajuga decumbens* Thunb, and *Ajuga reptans,* the plants belonging to the genus Leonurus are *Leonurus sibiricus* Linne and *Leonurus macranthus* Maxim., the plants belonging to the genus Perilla are *Perilla frutescens* Britton var. *acuta* Kudo, *Perilla frutescens* Britton var. *acuta* Kudo forma viridis Makino, *Perilla frutescens* Britton var. *crispa* Decne, *Perilla frutescens* Britton var. *japonica* Hara and *Perilla frutescens* Britton var. *citriodora* Ohwi, the plant belonging to the genus Prunella is *Prunella vulgaris* L. var. *lilacina* Nakai, the plant belonging to the genus Schizonepeta is *Schizonepeta tenuifolia* Briquet, the plant belonging to the genus Rosmarinus is *Rosmarinus officinalis* Linne, the plants belonging to the genus Scutellaria are *Scutellaria baicalensis* Georgi and *Scutellaria indica* L., the plant belonging to the genus Lavandula is *Lavandula angustifolia* Moench., the plant belonging to the genus Ocimum is *Ocimum basillicum* L. and *Ocimum scanctum,* the plants belonging to the genus Thymus are *Thymus vulgaris* L. and *Thymus quinquecostatus* Celak., and the plants belonging to the genus Salvia are *Salvia officinalis* L. and *Salvia miltiorrhiza* Bunge.

4. The composition according to claim 1 wherein the cell or tissue of a mammal is human epidermic cell or human epidermis, respectively.

5. A method for enhancing hyaluronic acid productivity in a cell or tissue of a mammal, which comprises percutaneously administering to the mammal a composition comprising an extract of at least one plant belonging to the family Labiatae in an amount enough to accelerate the production of hyaluronic acid, and cosmetically or pharmaceutically acceptable carriers, diluents or auxiliaries.

6. The method according to claim 5 wherein the plant belonging to the family Labiatae is at least one selected from the group consisting of plants belonging to the genus Isodon, the genus Origanum, the genus Mentha, the genus Ajuga, the genus Leonurus, the genus Perilla, the genus Prunella, the genus Schizonepeta, the genus Rosmarinus, the genus Scutellaria, the genus Lavandula, the genus Ocimum, the genus Thymus and the genus Salvia.

7. The method according to claim 6 wherein the plants belonging to the genus Isodon are *Isodon japonicus* Hara and *Isodon trichocarpus* Kudo, the plant belonging to the genus Origanum is *Origanum majorana* L., the plants belonging to the genus Mentha are *Mentha piperita* L., *Mentha viridis* L. and *Mentha suaveolens,* the plants belonging to the genus Ajuga are *Ajuga decumbens* Thunb, and *Ajuga reptans,* the plants belonging to the genus Leonurus are *Leonurus sibiricus* Linne and *Leonurus macranthus* Maxim., the plants belonging to the genus Perilla are *Perilla frutescens* Britton var. *acuta* Kudo, *Perilla frutescens* Britton var. *acuta* Kudo forma viridis Makino, *Perilla frutescens* Britton var. *crispa* Decne, *Perilla frutescens* Britton var. *japonica* Hara and *Perilla frutescens* Britton var. *citriodora* Ohwi, the plant belonging to the genus Prunella is *Prunella vulgaris* L. var. *lilacina* Nakai, the plant belonging to the genus Schizonepeta is *Schizonepeta tenuifolia* Briquet, the plant belonging to the genus Rosmarinus is *Rosmarinus officinalis* Linne, the plants belonging to the genus Scutellaria is *Scutellaria baicalensis* Georgi and *Scutellaria indica* L., the plant belonging to the genus Lavandula is *Lavandula angustifolia* Moench., the plant belonging to the genus Ocimum is *Ocimum basillicum* L. and *Ocimum scanctum,* the plants belonging to the genus Thymus are *Thymus vulgaris* L. and *Thymus quinquecostatus* Celak., and the plants belonging to the genus Salvia are *Salvia officinalis* L. and *Salvia miltiorrhiza* Bunge.

8. The method according to claim 5 wherein the cell or tissue of a mammal is human epidermic cell or human epidermis, respectively, and the composition is administered to human skin.

9. A composition suitable for topical application to mammalian skin, which comprises an extract of at least one plant belonging to the family Labiatae, selected from the group consisting of *Mentha viridis* L. and *Mentha suaveolens* belonging to the genus Mentha, *Ajuga reptans* belonging to the genus Ajuga, *Leonurus macranthus* Maxim, belonging to the genus Leonurus, and *Perilla frutescens* Britton var. *japonica* Hara and *Perilla frutescens* Britton var. *citriodora* Ohwi belonging to the genus Perilla, in an amount enough to accelerate the production of hyaluronic acid in a cell or tissue of the mammal, and cosmetically or pharmaceutically acceptable carriers, diluents or auxiliaries.

10. The composition according to claim 9 wherein the mammal is a human.

11. A process for preparing a composition for enhancing hyaluronic acid productivity in a cell or tissue in a mammal, which comprises mixing an extract of at least one plant belonging to the family Labiatae in an amount enough to accelerate the production of hyaluronic acid, homogeneously with cosmetically or pharmaceutically acceptable carriers, diluents or auxiliaries.

* * * * *